US005993861A

United States Patent [19]

Fogel

[11] Patent Number: 5,993,861

[45] Date of Patent: Nov. 30, 1999

[54] 12-HYDROXY STEARIC ACID ESTERS, COMPOSITIONS BASED UPON SAME AND METHODS OF USING AND MAKING SUCH COMPOSITIONS

[75] Inventor: Arnold W. Fogel, Upper Saddle River, N.J.

[73] Assignee: Bernel Chemical Co., Inc., Englewood, N.J.

[21] Appl. No.: 09/233,416

[22] Filed: Jan. 19, 1999

Related U.S. Application Data

[63] Continuation-in-part of application No. 09/009,659, Jan. 20, 1998.

[51] Int. Cl.$^6$ .................................................. A61R 31/20

[52] U.S. Cl. .......................................... 424/502; 516/919

[58] Field of Search ............................. 424/502; 516/919

[56] References Cited

U.S. PATENT DOCUMENTS

| | | |
|---|---|---|
| 3,687,883 | 8/1972 | Korf . |
| 4,074,978 | 2/1978 | Panzer . |
| 4,184,978 | 1/1980 | France et al. . |
| 4,228,151 | 10/1980 | Lange et al. . |
| 4,534,963 | 8/1985 | Gordon . |
| 5,025,004 | 6/1991 | Wu et al. . |
| 5,221,286 | 6/1993 | Singleton . |
| 5,436,006 | 7/1995 | Hirose et al. . |
| 5,451,254 | 9/1995 | Andrean et al. . |
| 5,476,648 | 12/1995 | Fogel . |
| 5,525,588 | 6/1996 | Michetti . |
| 5,620,682 | 4/1997 | Fogel . |
| 5,658,575 | 8/1997 | Ribier et al. . |
| 5,660,865 | 8/1997 | Pedersen et al. . |
| 5,674,475 | 10/1997 | Dahms et al. . |
| 5,690,918 | 11/1997 | Jacks et al. . |
| 5,730,893 | 3/1998 | Wyman et al. . |
| 5,785,979 | 7/1998 | Wells . |

*Primary Examiner*—James H. Reamer
*Attorney, Agent, or Firm*—Henry D. Coleman; R. Neil Sudol

[57] ABSTRACT

The present invention relates to a synthetic, branched chain, oil soluble, fatty acid esters which, when preferably partially neutralized in situ, is revealed as a new water-in-oil emulsifier. Formulations are presented which demonstrate a method for using the disclosed emulsifier to prepare stable water-in-oil emulsions of varying polarity and viscosity for use in a variety of dermatological applications, and/or wherever emulsions according to the present invention may be used.

64 Claims, No Drawings

12-HYDROXY STEARIC ACID ESTERS, COMPOSITIONS BASED UPON SAME AND METHODS OF USING AND MAKING SUCH COMPOSITIONS

RELATED APPLICATIONS

This application is a continuation-in-part application of application Ser. No. 09/009,659 of same title, filed Jan. 20, 1998.

FIELD OF THE INVENTION

The present invention relates to synthetic, branched chain, oil soluble, fatty acid esters which, when preferably partially neutralized in situ, is revealed as a new water-in-oil emulsifier. Formulations are presented which demonstrate a method for using the disclosed emulsifier to prepare stable water-in-oil emulsions of varying polarity and viscosity for use in a variety of dermatological applications, and/or wherever this type of emulsion may be useful.

BACKGROUND OF THE INVENTION

Since 1957 for the inventor, and much earlier for the art, the use of a beeswax-borax system to prepare a water-in-oil emulsion has been available in the art. This is a classical method for preparing water-in-oil emulsions, i.e, which generally comprise at least about ⅔ by weight of an oil phase and no more than about ⅓ by weight of a water phase. Typically, prior art emulsions of this type comprise about 9–10% by weight of beeswax in the oil phase and about 1% Borax NF in the water phase. The oils used to produce the oil phase include mineral oil and petrolatum and viscosity was built with paraffin and other waxes such ozokerite in minor amounts.

According to the Merck index, beeswax is comprised of approximately 22–25% by weight of a 36 carbon acid. In addition, beeswax generally comprises approximately 25% by weight $C_{35}$–$C_{36}$ alkanes and approximately 50% by weight of $C_{35}$–$C_{36}$ esters. Using beeswax, in the traditional water-in-oil emulsion, the acid and borax together form a "soap" emulsifier in situ which facilitates formation of the water-in-oil emulsion. Although the system functions reasonably well, problems emerge as beeswax may vary in componentry from batch to batch and produce quality control problems. In addition, compositions which utilize beeswax often require strenuous mixing or homogenization to facilitate the production of a stable final formulation.

Since 1982, the present inventor worked with 12-hydroxystearic acid to prepare solid di-fatty esters such as 12-stearoyl, stearyl and stearate. One of the first products synthesized in this series was a "tri fatty" solid emollient which is still sold under the tradename Hetester SSS.

After almost 40 years of research, the present inventor tried to make a $C_{36}$ then a $C_{40}$ acid to mimic beeswax in the latter's ability to form water-in-oil emulsion compositions, but without the other "solids" present in beeswax, which he identified as possibly being responsible for certain non-optimal characteristics of these compositions. In addition, it was surmised that the synthesis of a synthetic beeswax fatty acid would be more controllable and therefore would result in more accurate quality control ("QC") during processing.

OBJECTS OF THE INVENTION

It is an object of the invention to provide 12-hydroxy stearic acid esters which function as emulsifiers to provide storage stable water-in-oil emulsions.

It is an additional object of the invention to provide a method of making water-in-oil emulsions which are easy to formulate, are self-homogenizing and provide for accurate quality control.

It is yet another object of the invention to provide water-in-oil emulsions which can be used to readily manufacture personal care products including cosmetic products such as lipsticks as well as a myriad of types of creams and lotions.

It is still another object of the invention to provide water-in-oil emulsion compositions which exhibit significantly greater storage stability than those compositions of the prior art which include beeswax.

These and other objects of the invention may be readily gleaned from the detailed description of the invention which follows.

BRIEF DESCRIPTION OF THE PRESENT INVENTION

The present invention relates to 12-hydroxystearic acid ester compounds of the structure:

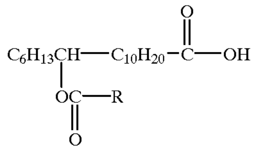

Where R is a linear or branch chained saturated or unsaturated $C_6$–$C_{35}$ hydrocarbon group, more preferably a $C_{11}$–$C_{23}$hydrocarbon group. Most preferably, R is a $C_{21}$–$H_{43}$group (such that the emulsifier is the behenoyl ester of 1 2-hydroxystearic acid or behenoyl stearic acid, "BSA").

The present 12-hydroxystearic acid esters may be utilized to produce water-in-oil emulsions for use as personal care products, such as creams and lotions, including pigmented formulations and as substitutes for beeswax in water-in-oil emulsions. The present compounds find particular use in emulsions, such as pigmented emulsions or moisturizing emulsions, among numerous others. These compounds provide excellent emulsification and, quite unexpectedly, are also excellent emollients. In many instances, the present compounds also plasticize the oils which are present in water-in-oil emulsion compositions to leave a dry, waxy feel rather than a predominantly oily, greasy feel. This unique feel is an unexpectedly favorable characteristic of water-in-oil emulsions according to the present invention.

Compositions based upon the present compounds exhibit consistent manufacture, thus obviating the quality control problems which occur when beeswax is used in traditional formulations. In addition, many of the compositions which are produced using the present compound are self-homogenizing, i.e., they are relatively easy to mix into a consistent formulation, without reliance on high speed sheer forces or other strenuous methods of mixing. Moreover, the water-in-oil emulsions according to the present invention exhibit unexpectedly favorable storage stability even at high temperatures (50° C.). This is a particularly advantageous feature compared to water-in-oil emulsions which have shown storage instability (i.e., separation into phases upon storage) leading to limited commercial application.

Emulsion compositions according to the present invention remain significantly more stable without separation at high temperatures (50° C.) compared to prior art compositions which utilize beeswax in the formulation.

Water-in-oil emulsion compositions according to the present invention comprise an oil phase and a water phase, with the oil phase generally ranging from about 10% to about 90% by weight of the water-in-oil emulsion composition and the water phase ranging from about 10% to about 90% by weight of the water-in-oil emulsion composition. More preferably, the oil phase in the composition ranges from about 25% to about 80% by weight of said composition, even more preferably about 40% to about 75% by weight of said composition, even more preferably about 50–60% to about 75% by weight, still more preferably about 65 to 70% by weight, and most preferably about 66–67% (about ⅔) by weight of said composition. The water phase (such phase including the borax-containing compound or related compound which reacts with the 12-hydroxystearic acid ester in the oil phase to produce an oil soluble salt upon mixing the water and oil phases) in the water-in-oil emulsion compositions according to the present invention comprises about 10% to about 90% by weight, preferably about 20% to about 75% by weight, more preferably about 25 to about 60% by weight, even more preferably, about 25% to about 40–50% by weight, still more preferably about 30 to about 35% by weight, most preferably about 33–34% (about ⅓) by weight of the emulsion composition.

In the present invention, the oil phase comprises an oil in a major amount (i.e., greater than about 50% by weight, more preferably at least about 70% and even more preferably about 75 to about 99.75% by weight of the oil phase) and as a minor component a hydroxystearic acid ester compound according to the chemical structure:

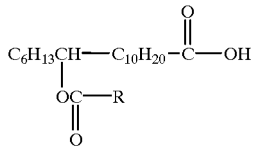

Where R is a linear or branch chained saturated or unsaturated $C_6$–$C_{35}$ more preferably, a $C_{11}$–$C_{24}$ hydrocarbon group, even more preferably, a $C_{21}H_{43}$ group, as a minor component (i.e., less than about 50% by weight). Thus, in the present invention the hydroxystearic acid ester preferably comprises about 0.25% to about 30% by weight of the oil phase, more preferably, about 0.5% to about 20% by weight of the oil phase, even more preferably about 1.0% to about 10% by weight of the oil phase, and even more preferably about 1% to about 7.5% by weight of the oil phase. The amount of oil in the oil phase preferably ranges from about 70% to about 99.75% by weight, more preferably, about 80% to about 99.5% by weight, even more preferably about 92.5% to about 99% by weight. It is noted here that the amount of the hydroxystearic acid ester compound and oil to be included within the oil phase will vary depending upon the amount of water to be included in the water-in-oil emulsion composition. As the amount of water increases in the emulsion composition, the amount of the hydroxystearic acid ester which is included in the emulsion composition also generally increases and the amount of oil decreases, as does the inversion temperature.

In addition to water, the water phase may also include an amount of a "neutralizing agent or compound" effective to produce an emulsion when the water phase and oil phases are combined. Examples of such compounds include, for example, boron-containing compounds such as sodium tetraborate decahydrate (Borax NF), sodium tetraborate tetrahydrate, $Ca(OH)_2$, $Mg(OH)_2$, $Al(OH)_3$, disodium monohydrogen phosphate or dipotassium monohydrogen phosphate (i.e., $Na_2HPO_4$ or $K_2HPO_4$), trisodium phsophate or tripotassium phosphate ($Na_3PO_4$ or $K_3PO_4$), $NaHCO_3$, $KHCO_3$, $Na_2CO_3$, $K_2CO_3$, NaOH and KOH (preferably, buffered NaOH and KOH) and fatty amine compounds (i.e., primary, secondary and tertiary amine compounds containing at least one $C_{10}$ to $C_{22}$ alkyl, alkene or substituted alkyl or alkene group).

Emulsion compositions according to the present invention may also include optional additives, for example, fragrances, preservatives, anti-oxidants, vitamins, pigments, conditioning agents, among numerous other standard cosmetic additives. These additives may be included in emulsion compositions according to the present invention in amounts up to about 25% by weight, preferably, in amounts ranging from about 0.01% to about 10% by weight, most preferably less than about 5% by weight within this range.

DETAILED DESCRIPTION OF THE INVENTION

The terms "emulsion" and "water-in-oil emulsion" are used synonymously throughout the specification to describe compositions according to the present invention. An "emulsion" according to the present invention is a cream or lotion which is generally formed by the suspension of a very finely divided liquid, in this case water, in another liquid, in this case, an oil. In the present invention, an emulsion is formed when the water phase is compatibilized in the oil phase, such that the water phase becomes "hidden" within the oil phase. While not being limited by way of theory, it is believed that in the water-in-oil emulsion compositions according to the present invention, the oil phase produces a liposome- or encapsulation-like structure or a related structure surrounding water and/or the water phase, with the reaction product of the 12-hydroxy stearic acid ester and neutralizing compound serving to enhance the formation of the liposome-like structure and consequently, the emulsion composition. The term emulsion is used to distinguish the present compositions from compositions which contain at least two distinct phases, i.e., an oil phase and a water phase.

The term "hydrocarbon" is used throughout the specification to describe R groups according to the present invention. R may be a linear or branch chained saturated or unsaturated $C_6$–$C_{35}$ hydrocarbon group, more preferably, a $C_{11}$–$C_{24}$ hydrocarbon group, even more preferably, a $C_{21}$–$H_{43}$ group. The term hydrocarbon embraces, but is not limited to, for example, alkyl, alkene groups (including those groups containg more than one unsaturated double bond), alkyne groups, aryl groups, aralkyl groups and related groups which are comprised of carbon and hydrogen atoms. Groups which may be found on fatty amines according to the present invention also may be described as hydrocarbons, although the number of carbon atoms which are found in hydrocarbon groups in the fatty amine according to the present invention falls within a more narrow range than do the hydrocarbon groups which may be used as R groups in stearic acid esters or emulsifiers according to the present invention.

The term "inversion temperature" is used throughout the specification to describe a temperature at which emulsion formation occurs with stability. Emulsion compositions according to the present invention generally have inversion temperatures of at least about 40° C., more preferably about 50° C. or higher.

The term "oil" is used throughout the specification to describe any of various lubricious, hydrophobic and combustible substances obtained from animal, vegetable and mineral matter. Oils for use in the present invention may include petroleum-based oil derivatives such as purified petrolatum and mineral oil. Petroleum-derived oils include aliphatic or wax-based oils, aromatic or asphalt-based oils and mixed base oils and may include relatively polar and non-polar oils. "Non-polar" oils are generally oils such as petrolatum or mineral oil or its derivatives which are hydrocarbons and are more hydrophobic and lipophilic compared to synthetic oils, such as esters, which may be referred to as "polar" oils. It is understood that within the class of oils, that the use of the terms "non-polar" and "polar" are relative within this very hydrophobic and lipophilic class, and all of the oils tend to be much more hydrophobic and lipophilic than the water phase which is used in the present invention.

In addition to the above-described oils, certain essential oils derived from plants such as volatile liquids derived from flowers, stems and leaves and other parts of the plant which may include terpenoids and other natural products including triglycerides may also be considered oils for purposes of the present invention.

Petrolatum (mineral fat, petroleum jelly or mineral jelly) and mineral oil products for use in the present invention may be obtained from a variety of suppliers. These products may range widely in viscosity and other physical and chemical characteristics such as molecular weight and purity. Preferred petrolatum and mineral oil for use in the present invention are those which exhibit significant utility in cosmetic and pharmacuetical products. Cosmetic grade oils are preferred oils for use in the present invention.

Additional oils for use in the present invention may include, for example, mono-, di- and tri-glycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from seeds or nuts and include drying oils, for example, linseed, iticica and tung, among others; semi-drying oils, for example, soybean, sunflower, safflower and cottonseed oil; non-drying oils, for example castor and coconut oil; and other oils, such as those used in soap, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other acceptable cosmetic emollient.

Preferred oils for use in the present invention include petrolatum, mineral oil or mixtures of petrolatum and mineral oil where the amount of petrolatum to mineral oil (on a weight/weight basis) ranges from about 1:20 to about 10:1, preferably about 1:5 to about 5:1, more preferably about 1:3 to about 1:1, depending upon the end use of the emulsion composition. The inclusion of petrolatum and/or mineral oil and/or the ratio of petrolatum to mineral oil in the present compositions will greatly influence the final viscosity of the water-in-oil compositions according to the present invention.

The term "storage stability" is used throughout the specification to describe an unexpected characteristic of emulsion compositions according to the present invention which relates to the fact that the present emulsions are generally storage stable at 50° C. for a period of at least about three months, and often longer than six months, a year or even longer. This is a particularly advantageous feature of emulsion compositions according to the present invention in comparison to prior art compositions, especially those which utilize beeswax to form the emulsion. Those prior art compositions tend to separate into at least two separate phases, generally a water phase and an oil phase within a relatively short period at a temperature at or above about 50° C.

The term "carboxylic acid reactive neutralizing agent or compound" or "neutralizing compound" is used throughout the specification to describe a compound which is reactive with the carboxylic acid group of the stearic acid ester to produce a salt or complex of the carboxylic acid in an amount effective to produce a stable emulsion when the water phase and oil phases are combined. In the present invention, the neutralizing agent or compound reacts or complexes with the carboxylic acid moiety of the 12-hydroxy stearic acid ester compound. A neutralizing compound for use in the present invention may be any alkaline compound which forms a hydrophobic/lipophilic soap (salt) with the 12-hydroxy stearic acid ester compound. In certain embodiments according to the present invention, preferred neutralizing compounds include any alkaline salt whose 5% aqueous solution gives a pH ranging from about 8 to about 12, preferably about 9–11. Preferred alkaline salts include, for example, $Na_2HPO_4$ or $K_2HPO_4Na_3PO_4$, $K_3PO_4$, $NaHCO_3$, $KHCO_3$, $Na_2CO_3$, $K_2CO_3$, and mixtures thereof, among others. In the present invention, the amount of neutralizing compound to 12-hydroxy stearic acid ester compound used in the final emulsion composition ranges from about 1 part (weight/weight) to 10 to about 2 parts to 1, more preferably about 1:4 to about 1:1, more preferably about 1:2. The amount of neutralizing compound to 12-hydroxy stearic acid ester compound used in the present compositions is not necessarily a stoichiometric amount. It is noted that this amount should serve as a guide, but not to limit, the understanding as to the amount of neutralizing compound to be used in the present invention. Examples of preferred neutralizing compounds include, for example, boron-containing compounds such as sodium tetraborate decahydrate (Borax NF), sodium tetraborate tetrahydrate, tetrahydroxy boron, boron monoxide (which converts to tetrahydroxy boron on reactions with water), $Ca(OH)_2$, $Mg(OH)_2$, $Al(OH)_2$, $Na_2HPO_4$ or $K_2HPO_4$ $Na_3PO_4$, $K_3PO_4$, $NaHCO_3$, $KHCO_3$, $Na_2CO_3$, $K_2CO_3$, NaOH, KOH and fatty amine compounds (i.e., primary, secondary and tertiary amine compounds containing at least one $C_{10}$ to $C_{22}$ alkyl group) and mixtures thereof, especially mixtures of the previously described phosphate and carbonate salts. Preferred neutralizing compounds which are used in the present invention include, for example, sodium tetraborate decahydrate (Borax NF) and sodium tetraborate tetrahydrate, with sodium tetraborate decahydrate (Borax NF) being the preferred compatibilizing agent for use in the present invention.

The term "self-emulsifier" or "self-emulsification" is used to describe compounds according to the present invention which are the reaction products of a 12-hydroxy stearic acid ester compound and a neutralizing compound according to the present invention and may be used to create emulsion compositions according to the present invention by simple mixing, i.e., without relying on shear forces or high speed mixing action. These emulsifiers may be created in situ by mixing the 12-hydroxy stearic acid ester with the neutralizng compound during formation of the emulsion, or alternatively, may be prepared separately, by neutralizing the 12-hydroxy stearic acid ester with the neutralizing compound and then adding the pre-formed emulsifier to other components to form the emulsion composition.

The term “secondary emulsifier” or “helper emulsifer” is used throughout the specification to describe compounds which are added to the emulsifier compositions according to the present invention to provide a more stable and in some embodiments consistent emulsion composition. Secondary or helper emulsifiers may be particularly advantageous when formulating emulsions compositions which utilize one or more salts such as phosphate salts or carbonate salts to neutralize the srtearic acid ester. Emulsifiers as used generally are considered surfactants which exhibit good surface activity and produce a low interfacial tension in the system in which it is used. Secondary emulsifiers preferably used in the present invention exhibit a tendency to migrate to the interface, rather than remain dissolved in either one of the water or emollient oil phase. Mixtures of secondary emulsifiers actually may be preferred in certain embodiments, where the need is to provide better interaction between the oil and water phases. Secondary emulsifiers have been advantageously used in the present invention where the neutralizing agent is or contains at least one phosphate or carbonate salt, or where the oil is a synthetic ester or more polar oil. One of ordinary skill in the art may readily determine the type of emulsifier or emulsifying system (group of emulsifiers) which may be used in the water-in-oil emulsions according to the present invention. A secondary emulsifier is used in the present invention in an amount effective to aid or promote emulsification of the water phase and oil phase (“emulsification effective amount”). As a general rule, the amount of secondary emulsifer which is included in compositions according to the present invention ranges from about 0.01% to about 10% by weight, more preferably about 0.1% to about 5.0% by weight of the final emulsion composition. In emulsion compositions according to the present invention, where secondary emulsifiers are optionally included, the weight ratio of 12-hydroxystearic acid esters to secondary emulsifier ranges from about 20:1 to about 1:20, more preferably about 10:1 to about 1:1.

Exemplary secondary emulsifiers for use in the present invention may be any cosmetically acceptable oil soluble non-ionic or anionic (and in rare instances quaternary or amphoteric) surfactant which has a hydrophilic group (“tail”) at one end of the molecule, of which polyethylene glycol 1500 dihydroxystearate (Arlacel P135®, available from ICI Americas, Inc) and diethanolamine cetyl phosphate (Amphisol®, available from Givaudin-Roure, division of Roche, Inc.) are particularly preferred, although a large number of other secondary emulsifiers may be used in the present invention. One of ordinary skill will understand to include one or more secondary emulsifiers in emulsion compositions according to the present invention in order to facilitate and enhance interaction of the water and oil phases.

In addition to 12-hydroxy stearic acid ester compounds, an oil, water and neutralizng compound, the emulsion compositions may also comprise, in amounts totalling up to about 25% by weight of the total emulsion composition, preferably comprising about 0.001% to about 10% by weight, even more preferably no more than about 5% by weight within this range, of one or more optional additive selected from one or more secondary emulsifier, fragrances, preservatives, anti-oxidants, vitamins, pigments, conditioning agents, among numerous other standard cosmetic additives.

12-Hydroxy stearic acid ester compounds according to the present invention are generally made by reacting 12-hydroxy stearic acid with another carboxylic acid (depending upon the length and degree of unsaturation of the carboxylic acid which is reacted to form the ester group at the 12 hydroxyl position) in the presence of an effective amount of a catalyst (the amount can range from 0.005% to 1% or more by weight of the 12-hydroxy stearic acid and other carboxylic acid reactant used) such as dibutyl tin oxide or tin oxalate, among numerous others. In a preferred method, stoichiometric amounts (i.e., a 1:1 molar ratio) of the reactants are combined with the catalyst in a reaction chamber which will allow ample heat to be added to the mixture (the temperature of the reaction may vary depending upon the rate of reaction desired, but will preferably be above about 200° C.) and water to be removed (as the esterification reaction proceeds). The reaction mixture is heated until a desired saponification value is obtained evidencing completeness of the reaction. Upon cooling the reaction mixture, the stearic acid ester compound is readily separated from impurities, by extraction, fractionation (under reduced pressure), simple crystrallization or related techniques which are all well known in the art. Preferably, the stearic acid ester is obtained in quantitative or near quantitative yields.

Emulsion compositions according to the present invention may be made by mixing the individual components in any order at elevated temperature, but are preferably made by first preparing the oil phase and water phase at elevated temperature (preferably, above about 70–75° C., more preferably above about 85° C.) separately, then combining the oil phase with the water phase also at an elevated temperature (preferably, by adding the water phase to the oil phase) such that the oil phase remains soluble within itself during mixing. Generally, the temperature at which mixing is effected is preferably at least about 50° C., more preferably at least about 65 to 75° C., even more preferably at least about 75 to 85° C., and most preferably at least about 85° C. These are temperatures which are generally effective to allow the oil phase to remain soluble within itself (at a temperature wherein the oil phase remains clear and in a solution) during mixing. After mixing for at least about 10–15 minutes, more preferably at least 30 minutes or more (depending upon batch size) at elevated temperatures, the mixture is then cooled before use and/or packaging. Mixing is generally performed in a simple propeller mixer with vortex formation without the application of high shear force. Although one could use higher mixing speeds, the self-emulsifiers which are used make mixing the compositions relatively easy. All components may be mixed together in a one pot preparation, or one or more components (such as the oil phase, water phase or emulsifier) may be prepared separately and then combined. In preferred embodiments, after the separate water and oil phases are prepared, the water phase is added to the oil phase and the combined phases are mixed thoroughly for maximum result. It is noted that the preferred method for making the present composition comprises first making the water and oil phases separately, preferably adding the water phase to the oil phase, followed by mixing the phases together, all at elevated temperature. Alternatively, it is possible to separately mix the individual components in a single pot preparation or prepare the complex of the stearic acid ester compound and the neutralizing compound before it is added to the oil and/or water phases.

It is noted that the 12-behenoyl stearic acid (BSA, also known by the names 12-(behenoyloxy)stearic acid and 12-(decosanoyloxy)octadenaoic acid ) is more efficient at producing an emulsion with non-polar oils (such as mineral oil or petrolatum) or emollients than it is with polar oils (such as fatty esters, etc.) or emollients. In certain instances, when utilizing polar oils or emollients, either alone or in combination with a non-polar oil, at least one additional secondary or helper emulsifier may be advantageously added to produce a superior emulsion composition. In certain embodiments, therefore, the inclusion of a secondary emulsifer may be advantageously employed. Preferred secondary emulsifiers for inclusion in the present emulsion compositions include for example, polyethyleneglycol 1500 dihydroxystearate (Arlacel P135®'", available from ICI Americas, Inc.) and diethanolaminecetyl phosphate (Amphisol®, available from Givaudin-Roure), in amounts generally ranging from about 0.01% to about 10% (up to aobut 20% by weight of the final emulsion composition), more preferably about 0.1% to about 5%, by weight of the final emulsion composition.

Emulsion compositions according to the present invention have inversion temperatures of at least about 40–45° C., preferably at least about 50° C., more preferably at least about 60° C. or higher. Inversion temperatures of at least about 65 ° C. may be particularly preferred. The higher the inversion temperature of an emulsion composition according to the present invention, generally, the more stable is the emulsion composition.

Having generally described the invention, reference is now made to the following examples which are intended to illustrate preferred embodiments and comparisons but which are not to be construed as limiting to the scope of this invention as is more broadly set forth above and in the appended claims.

EXAMPLES

Example I

Synthesis of 12-Behenoyl Hydroxystearic Acid (BSA)

Materials 1 mole Behenic acid 1 mole 12-Hydroxy Stearic acid 0.1% w/w Dibutyl Tin Oxide (Based upon total weight of reactants).

Procedure

In a glass vessel, equipped with proper mixing and a water trap to collect water, combine all ingredients. Mix and heat at 200° C. until desired saponification value, hydroxyl value and acid value are achieved.

| Typical Assay for BSA | | |
|---|---|---|
| sap value | = | 161.5 |
| acid value | = | 104.5 |
| hydroxyl value | = | 7.5 |
| color (melted) | = | gardner 2+ |
| melting point | = | 68° C. |

BSA is the common cosmetic label name. BSA also goes by the names 12-(behenoyloxy)stearic acid and 12-(decosanoyloxy)octadenaoic acid.

Example II

Water-in-Oil Flowing Lotion Based Upon Non-Polar Oils

The following components were combined in two separate phases, phase A, the oil phase and phase B, the water phase. After complete mixing of components to produce each sof the individual phases in the amounts as set forth below, the two phases are combined under elevated temperature (85° C.) and mixing to produce a flowing lotion.

| | | Weight % | |
|---|---|---|---|
| Phase A: | "BSA" | 2.3 | |
| (heat to 85° C. | White Petrolatum | 10.0 | |
| and mix) | (Kaydol) Mineral oil | 53.2 | |
| | Propyl Paraben | 0.1 | |
| Phase B: | Water, deionized | 33.3 | |
| | Borax N.F. | 1.1 | |
| | | 100.0% | total |

The procedure used was as follows:

Phase B was added to phase A @85° C.—the combined phases were mixed and cooled without aeration to 45–50° C.—package.

Note: In the case of this emulsion, the "BSA" is the primary and only emulsifier used. The use of about a 5:1 ratio of mineral oil to petrolatum produced a free-flowing lotion.

Kaydol- type of mineral oil obtained from Witco, Inc.

Example III

Water-in-Oil Cream Based upon Polar and Non-Polar Oils

The same procedure which was followed for Example II was also followed here, except that phase C was added after phases A and B were thoroughly mixed.

| | | Weight % | |
|---|---|---|---|
| Phase A: | "BSA" | 2.30 | |
| (heat to 85° C. | DiBehenyl Fumarate (1) | 8.00 | |
| and mix) | White Petrolatum | 10.00 | |
| | Mineral Oil (Kaydol) | 33.45 | |
| | Di-2-Ethyl Hexyl Fumarate (2) | 10.00 | |
| | DEA Cetyl Phosphate (amphisol) (3) | 0.50 | |
| | Propyl Paraben | 0.10 | |
| Phase B: | Water, deionized | 33.30 | |
| (heat to 85° C.) | Borax | 1.10 | |
| Phase C: | Fumed $SiO_2$ (cabosil) | 1.25 | |
| (add to emulsion at 75–80° C.) | | 100.0% | total |

(1) obtained by reacting 2 moles behenic alcohol with 1 mole fumaric acid using standard ester manufacturing procedures (heated at 160–180° C. with 10% by weight of the reactants of a catalyst such as tin oxalate or dibutyl tin oxide) in standard manufacturing equipment until an appropriate SAP value is reached.

(2) commercial as Bernel Ester 284 (Bernel Chemical Co., Englewood, New Jersey)

(3) Amphisol available from Hoffmann-LaRoche, Nutley, New Jersey.

Procedure

Add B to A at 85° C. Mix without aeration. Cool and add C at 75–80° C.; continue to mix until homogeneous and cool to approximately 55° C. Package at 55° C.

Note: the "BSA" from example 1 is the primary emulsifier, however, this emulsion uses 2 auxilliary emulsifiers with "BSA". They are amphisol and cabosil. The di-behenyl fumarate is a "thickener" in this composition.

Example IV

Synthetic Water-in-Oil Cream Based upon Polar Oils

The same procedure which was followed for Example III was essentially also followed here, with minor variation.

| | | Weight % | |
|---|---|---|---|
| phase A: | "BSA" | 2.30 | |
| (mix at | Di Behenyl Fumarate (1) | 8.00 | |
| 85–90° C.) | Di-$C_{12-15}$ Alkyl Fumarate (2) | 10.00 | |
| | Di-Decyl Tetra Decyl Fumarate (1) | 28.45 | |
| | (Octyl Dodecyl NeoPentanoate) | | |
| | ELEFAC I-205 | 15.00 | |
| | DEA Cetyl Phosphate (Amphisol) (3) | 0.50 | |
| | Propyl Paraben | 0.10 | |
| phase B: | Water, deionized | 33.30 | |
| (mix at | Borax N.F. | 1.10 | |
| 85–90° C.) | | | |
| phase C: | Fumed $SiO_2$ (cabosil) | 1.25 | |
| | | 100.0% | total |

(1) obtained as per example III;
(2) commercial as Marrix SF (Bernel Chemical Co., Englewood, New Jersey;
(3) Hoffmann-LaRoche Procedure Add B to A at 85° C. and mix without aeration. Continue mixing while slowly adding C. Mix and cool to 50° C. Package.

Example V

Comparison of Related Water-in-Oil Emulsion Compositions

A number of compositions were made to determine the levels of stearic acid ester at which stability is affected. The influence of mineral oil and petrolatum on stability was also determined. The results appear in Table 1, below. The compositions were made following the general procedure set forth in Example II, above. Essentially, the components of the oil phase, the behenyl stearic acid ester (BSA), the mineral oil and where applicable, petrolatum were combined in a phase A at elevated temperature (phase A also contained 0.1% by weight of propyl paraben dissolved in phase A as a preservative). To this phase A was added phase B, which included water and the Borax NF, also at elevated temperature (approximately 85 ° C.). The inversion temperature was determined by establishing at which temperature emulsion formation occurred (mixture becomes smooth and shiny evidencing the absence of two phases).

TABLE 1

| Example | % BSA | % Borax NF | % Water | % Mineral Oil | % Petrolatum | Inversion Temp. (° C.) |
|---|---|---|---|---|---|---|
| 1 | 2.3 | 1.1 | 33.3 | 40.0 | 23.3 | >68° C. |
| 2 | 5.0 | 2.4 | 50.0 | 42.5 | 0.0 | 56–52° |
| 3 | 7.5 | 3.6 | 65.1 | 23.1 | 0.0 | 46–43° |
| 4 | 1.7 | 0.8 | 17 | 40.4 | 40.0 | >68° C. |

BSA-12-Behenoyl Stearic Acid
All % are % by weight of the total emulsion composition.
Inversion Temperature-temperature at which stable emulsion occurs
pH's of the compositions are approximately 8.4.

Conclusion

1) As the percent by weight of BSA was increased, the amount of water which could be included within the composition and still form an emulsion increased. Likewise, as the amount of water incrases, the inversion temperature tends to decrase significantly.

2) The highest percent by weight of water which can be included in the emulsion compositions is approximately 75%.

3) The lowest percent by weight of water which can be included in the emulsion compositions is approximately 10%.

Note- In example 2 on the chart of Table 1, all ingredients alternatively alternatively were mixed together initially at room temperature (20–25° C) in a single pot method. The mixture was heated and mixed to 85° C., then with mixing and cooling, we obtained the same inversion temperature (56–52° C.) obtained by forming the emulsion by mixing two phases together at elevated temperature. This approach represents an alternative embodiment of the method of making the emulsions according to the present invention. In large production batches, the inventor believes that the water phase and oil phase should be prepared separately, preferably at a temperaturem of about 85° C. and then the water phase should be added to the oil phase at the elevated temperature in order to increase the solution of any compounds which might be insoluble in one of the phases.

Example VI

Mineral Oil System

The following components were combined in two separate phases, phase A, the oil phase and phase B, the water phase. After complete mixing of components to produce each of the individual phases in the amounts as set forth below (at 80° C., with mixing), the two phases are combined under elevated temperature (80° C.) and mixing to produce a flowing lotion.

| | | Weight % | |
|---|---|---|---|
| Phase A: | "BSA" | 5.0 | |
| (heat to 80° C. | (Kaydol) Mineral oil | 42.5 | |
| and mix) | Propyl Paraben | 0.1 | |
| Phase B: | Water, deionized | 50.0 | |
| | Borax N.F. | 2.4 | |
| | | 100.0% | total |

The procedure used was as follows:

Phase B was added to phase A @80° C.—the combined phases were mixed and cooled without aeration to 40° C.—package.

Note: In the case of this emulsion which used the non-polar mineral oil, the "BSA" is the primary and only emulsifier used.

Kaydol—type of mineral oil obtained from Witco, Inc.

Example VII

Petrolatum Cream

The following components were combined in two separate phases, phase A, the oil phase and phase B, the water phase. After complete mixing of components to produce each of the individual phases in the amounts as set forth below (at 80° C., with mixing), the two phases are combined under elevated temperature (80° C.) and mixing to produce a flowing lotion.

| | | Weight % | |
|---|---|---|---|
| Phase A: | "BSA" | 4.5 | |
| (heat to 80° C. | Petrolatum USP | 47.75 | |
| and mix) | Propyl Paraben | 0.1 | |
| Phase B: | Water, deionized | 45.50 | |
| | Borax N.F. | 2.10 | |
| | | 100.0% | total |

The procedure used was as follows:

Phase B was added to phase A @80° C.—the combined phases were mixed and cooled without aeration to 40° C.—package.

Note: In the case of this emulsion which used the non-polar mineral oil, the "BSA" is the primary and only emulsifier used.

Example VIII

Suntan Lotion-SPF 30 Waterproof

The same procedure which was followed for earlier examples was essentially also followed here, with minor variation.

| | | Weight % | |
|---|---|---|---|
| phase A: | "BSA" | 4.0 | |
| (mix at | Di Behenyl Fumarate (1) | 3.0 | |
| 80° C.) | Arlacel P135 ® | 2.0 | |
| | Capryl isostearate Beantree ™ (2) | 21.6 | |
| | ELEFAC I-205 (3) | 10.0 | |
| | Octyl Methoxy Cinnamate | 7.5 | |
| | Octyl Salicylate | 5.0 | |
| | Oxy Benzone | 5.0 | |
| | Propyl Paraben | 0.1 | |
| phase B: | Water, deionized | 40.0 | |
| (mix at | Borax N.F. | 1.8 | |
| 80° C.) | | 100.0% | total |

(1) obtained as per example III;
(2) commercial as Beantree from Bernel Chemical Co., , Englewood, New Jersey;
(3) Bernel Chemical Co.

Procedure

Add B to A at 80° C. and mix without aeration. Cool to 40° C. Package.

Example IX

Lotion Base Using Phosphate Salt as Neutralizing Agent

The same procedure which was followed for the earlier described examples was essentially also followed here, with minor variation.

-continued

| | | Weight % | |
|---|---|---|---|
| phase A: | "BSA"(1) | 5.0 | |
| (mix at 80° C.) | Arlacel P-135 | 5.0 | |
| | Capryl Isostearate (2) | 20.0 | |
| | Dibehenyl fumarate (3) | 3.0 | |
| phase B: | Water, deionized | 61.9 | |
| (mix at | Disodium Acid Phosphate | 5.0 | |
| 80° C.) | ($Na_2HPO_4$) | | |
| Phase C: | Kathon CG (4) | 0.1 | |
| | | 100.0% | total |

(1) obtained as per example III;
(2) commercial as Beantree (Bernel Chemical Co., Englewood, New Jersey);
(3) commercial as Marrix 222 ® (Bernel Chemical Co., Englewood, New Jersey);
(4) Rohm & Haas.

Procedure

Add B to A at 80° C. and mix until uniform. Cool to 70° C. and add Phase C. Continue mix and cool to 35–40° C. Package.

Example X

Petrolatum Cream Base Using Carbonate Salt as Neutralizing Agent

The same procedure which was followed for earlier examples was essentially also followed here, with minor variation.

| | | Weight % | |
|---|---|---|---|
| phase A: | "BSA" | 4.5 | |
| (mix at | Di Behenyl Fumarate (1) | 3.0 | |
| 80° C.) | Arlacel P-135 ® | 2.0 | |
| | Propyl Paraben | 0.1 | |
| | Petrolatum USP | 44.3 | |
| phase B: | Water, deionized | 44.1 | |
| (mix at | $Na_2CO_3$ | 1.0 | |
| 80° C.) | $NaHCO_3$ | 1.0 | |
| | | 100.0% | total |

Procedure

Add B to A at 80° C. and mix until uniform. Continue mix and cool to 40° C. Package.

It is to be understood by those skilled in the art that the foregoing description and examples are illustrative of practicing the present invention, but are in no way limiting. Variations of the detail presented herein may be made without departing from the spirit and scope of the present invention as defined by the following claims.

I claim:

1. An emulsifier compound for use in producing oil-in-water emulsions consisting essentially of the reaction product of a 12-hydroxystearic acid ester compound of the formula:

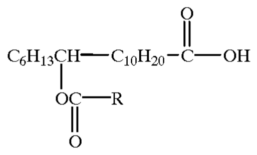

where R is a linear or branch chained saturated or unsaturated $C_6$–$C_{35}$ hydrocarbon group and a neutralizing compound selected from the group consisting of sodium tetraborate decahydrate, sodium tetraborate tetrahydrate, $Al(OH)_3$, $Ca(OH)_2$, $Mg(OH)_2$, $Na_2HPO_4$, $K_2HPO_4$, $Na_3PO_4$, $K_3PO_4$, $NaHCO_3$, $KHCO_3$, $Na_2CO_3$, $K_2CO_3$, NaOH, KOH, a fatty amine compound and mixtures, thereof.

2. The compound according to claim 1 wherein said fatty amine compound is a primary, secondary or tertiary amine compound containing at least one $C_{10}$ to $C_{22}$ alkyl, alkene or substituted alkyl or alkene group.

3. The emulsifier compound according to claim 2 wherein said fatty amine contains at least one $C_{10}$ to $C_{22}$ alkyl group.

4. The emulsifier compound according to claim 1 wherein said neutralizing compound is selected from group consisting of sodium tetraborate decahydrate and sodium tetraborate tetrahydrate.

5. The emulsifier compound according to claim 1 wherein R is a $C_{11}$–$C_{23}$ alkyl group.

6. The emulsifier compound according to claim 1 wherein said 12-hydroxystearic acid ester is 12-(behenoyloxy)stearic acid.

7. The emulsifer compound according to claim 1 wherein said neutralizing agent is selected from the group consisting of $Na_2HPO_4$, $K_2HPO_4$, $Na_3PO_4$, $K_3PO_4$, $NaHCO_3$, $KHCO_3$, $Na_2CO_3$, $K_2CO_3$ and mixtures, thereof.

8. An emulsifier compound for use in producing oil-in-water emulsions consisting essentially of the reaction product of a 12 hydroxystearic acid ester compound according to the formula:

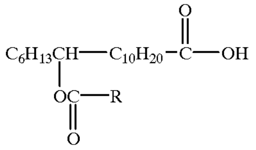

where R is a linear or branch chained saturated or unsaturated $C_6$–$C_{35}$ hydrocarbon group and a neutralizing compound is selected from the group consisting of sodium tetraborate decahydrate, sodium tetraborate tetrahydrate, $Na_2HPO_4$, $K_2HPO_4$, $Na_3PO_4$, $NaHCO_3$, $KHCO_3$, $Na_2CO_3$, $K_2CO_3$ and mixtures, thereof.

9. The compound according to claim 8 wherein said 12-hydroxystearic acid ester is 12-(behenoyloxy)stearic acid.

10. The compound according to claim 8 wherein said 12-hydroxystearic acid ester is 12-(behenoyloxy)stearic acid and said neutralizing compound is sodium tetraborate decahydrate.

11. A composition consisting essentially of: an oil phase and a water phase, said oil phase comprising about 10% to about 90% by weight of said composition and said water phase comprising about 10% to about 90% by weight of said composition, said oil phase consisting essentially of about 70% to about 99.75% by weight of an oil and about 0.25% to about 30% by weight of a 12-hydroxystearic acid ester compound according to the formula:

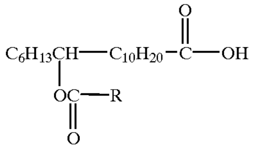

where R is a linear or branch chained saturated or unsaturated $C_6$–$C_{35}$ hydrocarbon group, said water phase consisting essentially of water and an amount of a neutralizing compound effective to produce an emulsion composition when said oil phase and said water phase are mixed.

12. The composition according to claim 11 wherein R is a $C_{11}$–$C_{23}$ hydrocarbon group.

13. The composition according to claim 11 wherein said neutralizing compound is selected from the group consisting of sodium tetraborate decahydrate, sodium tetraborate tetrahydrate, $Al(OH)_3$, $Mg(OH)_2$, $Ca(OH)_2$, $Na_2HPO_4$, $K_2HPO_4$, $Na_3PO_4$, $K_3PO_4$, $NaHCO_3$, $KHCO_3$, $Na_2CO_3$, $K_2CO_3$, NaOH, KOH, a fatty amine compound and mixtures thereof.

14. The composition according to claim 13 wherein said fatty amine compound is a primary, secondary or tertiary amine compound containing at least one $C_{10}$ to $C_{22}$ alkyl or alkene or substituted alkyl or alkene group.

15. The composition according to claim 13 wherein said neutralizing compound is selected from the group consisting of $Na_2HPO_4$, $K_2HPO_4$, $Na_3PO_4$, $K_3PO_4$, $NaHCO_3$, $KHCO_3$, $Na_2CO_3$, $K_2CO_3$ and mixtures thereof.

16. The composition according to claim 11 wherein said neutralizing compound is selected from group consisting of sodium tetraborate decahydrate and sodium tetraborate tetrahydrate.

17. The composition according to claim 11 where R is a $C_{11}$–$C_{23}$ hydrocarbon group.

18. The composition according to claim 11 wherein said 12-hydroxystearic acid ester is 12-(behenoyloxy)stearic acid.

19. The composition according to claim 11 wherein said oil comprises at least about 80% by weight of said oil phase and said stearic acid ester compound comprises no more than about 20% by weight of said oil phase.

20. The composition according to claim 11 wherein said oil phase further includes about 0.01% to about 20% by weight of a secondary emulsifier.

21. The composition according to claim 20 wherein said oil is a polar oil.

22. The composition according to claim 20 wherein said secondary emulsifier is selected from the group consisting of polyethylene glycol 1500 dihydroxystearate and diethanolamine cetyl phosphate in an amount ranging from about 0.15 to about 10% by weight of said emulsion composition.

23. The composition according to claim 20 wherein said neutralizing compound is selected from the group consisting of $Na_2HPO_4$, $K_2HPO_4$, $Na_3PO_4$, $K_3PO_4$, $NaHCO_3$, $KHCO_3$, $Na_2CO_3$, $K_2CO_3$ and mixtures thereof.

24. A composition consisting essentially of: an oil phase and a water phase, said oil phase comprising about 25% to about 80% by weight of said composition and said water phase comprising about 20% to about 75% by weight of said composition, said oil phase consisting essentially of about 80% to about 99.5% by weight of an oil and about 0.5% to about 20% by weight of a 12-hydroxystearic acid ester compound according to the formula:

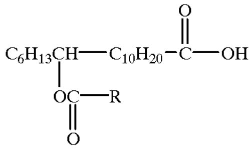

where R is a linear or branch chained saturated or unsaturated $C_{11}$–$C_{23}$ hydrocarbon group, said water phase consisting essentially of water and an amount of a neutralizing compound selected from the group consisting of sodium tetraborate decahydrate, sodium tetraborate, $Na_2HPO_4$, $K_2HPO_4$, $Na_3PO_4$, $K_3PO_4$, $NaHCO_3$, $KHCO_3$, $Na_2CO_3$, $K_2CO_3$ and mixtures thereof effective to produce an emulsion composition when said oil phase and said water phase are mixed.

25. The composition according to claim 24 wherein said oil phase further includes a secondary emulsifier in an amount ranging from about 0.1% to about 20% by weight.

26. The composition according to claim 24 wherein said oil is a polar oil.

27. The composition according to claim 24 wherein said secondary emulsifier is selected from the group consisting of polyethylene glycol 1500 dihydroxystearate and diethanolamine cetyl phosphate in an amount ranging from about 0.1% to about 10% by weight of said emulsion composition.

28. The composition according to claim 25 wherein said neutralizing compound is selected from the group consisting of $Na_2HPO_4$, $K_2HPO_4$, $Na_3PO_4$, $K_3PO_4$, $NaHCO_3$, $KHCO_3$, $Na_2CO_3$, $K_2CO_3$ and mixtures thereof.

29. The composition according to claim 24 further including up to about 25% by weight of at least one additive selected from the group consisting fragrances, preservatives, anti-oxidants, vitamins, pigments and conditioning agents.

30. The composition according to claim 24 wherein said 12-hydroxystearic acid ester is 12-(behenoyloxy)stearic acid and said oil is mineral oil, petrolatum or a mixture of mineral oil and petrolatum.

31. An emulsion composition consisting essentially of:

1) about 0.5% to about 15% by weight of the reaction product of a 12-hydroxy stearic acid ester compound according to the structure:

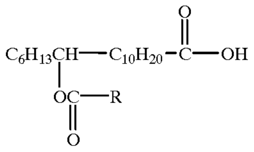

where R is a linear or branch chained saturated or unsaturated $C_6$–$C_{35}$ hydrocarbon group and a neutralizing compound selected from the group consisting of sodium tetraborate decahydrate, sodium tetraborate tetrahydrate, $Al(OH)_3$, $Ca(OH)_2$, $Mg(OH)_2$, $Na_2HPO_4$ or $K_2HPO_4Na_3PO_4$, $K_3PO_4$, $NaHCO_3$, $KHCO_3$, $Na_2CO_3$, $K_2CO_3$, NaOH, KOH, a fatty amine compound and mixtures thereof;

2) about 15% to about 89.5% by weight of an oil;

3) optionally, from 0.1% to about 20% by weight of a secondary emulsifier; and 4) about 10% to about 75% water.

32. The composition according to claim 31 wherein said R is a $C_{11}$–$C_{23}$ hydrocarbon group and said neutralizing agent is selected from the group consisting of sodium tetraborate decahydrate, sodium tetraborate tetrahydrate, $Na_2HPO_4$, $K_2HPO_4Na_3PO_4$, $K_3PO_4$, $NaHCO_3$, $KHCO_3$, $Na_2CO_3$, $K_2CO_3$, and mixtures thereof.

33. A composition consisting essentially of: an emulsion, said emulsion being formed by mixing an oil phase and a water phase, said oil phase comprising about 10% to about 90% by weight of said composition and said water phase comprising about 10% to about 90% by weight of said composition, said oil phase consisting essentially of at least about 70% to about 99.75% by weight of an oil and about 0.25% to about 30% by weight of a 12-hydroxystearic acid ester compound according to the formula:

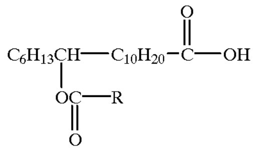

where R is a linear or branch chained saturated or unsaturated $C_6$–$C_{35}$ hydrocarbon group, said water phase consisting essentially of water and an amount of a neutralizing compound effective to produce an emulsion when said oil phase and said water phase are mixed.

34. The composition according to claim 33 wherein said neutralizing compound is selected from the group consisting of sodium tetraborate decahydrate, sodium tetraborate tetrahydrate, $Al(OH)_3$, $Ca(OH)_2$, $Mg(OH)_2$, $Na_2HPO_4$ or $K_2HPO_4Na_3PO_4$, $K_3PO_4$, $NaHCO_3$, $KHCO_3$, $Na_2CO_3$, $K_2CO_3$, NaOH, KOH, a fatty amine compound and mixtures thereof.

35. The composition according to claim 34 wherein said fatty amine compound is a primary, secondary or tertiary amine compound containing at least one $C_{10}$ to $C_{22}$ alkyl, alkylene or substituted alkyl or alkylene group.

36. The composition according to claim 35 wherein said fatty amine contains at least one $C_{10}$ to $C_{22}$ alkyl group.

37. The composition according to claim 33 wherein said neutralizing compound is selected from group consisting of sodium tetraborate decahydrate and sodium tetraborate tetrahydrate, $Na_2HPO_4$, $K_2HPO_4Na_3PO_4$, $K_3PO_4$, $NaHCO_3$, $KHCO_3$, $Na_2CO_3$, $K_2CO_3$, NaOH, KOH and mixtures thereof.

38. The composition according to claim 33 where R is a $C_{11}$–$C_{23}$ hydrocarbon group.

39. The composition according to claim 33 wherein said 12-hydroxystearic acid ester is 12-(behenoyloxy)stearic acid.

40. The composition according to claim 33 wherein said oil comprises at least about 80% by weight of said oil phase and said stearic acid ester compound comprises no more than about 20% by weight of said oil phase.

41. The composition according to claim 34 wherein said oil phase further includes a secondary emulsifier in an emulsification effective amount.

42. The composition according to claim 34 wherein said oil is a polar oil.

43. The composition according to claim 36 wherein said secondary emulsifier is selected from the group consisting of polyethylene glycol 1500 dihydroxystearate and diethanolamine cetyl phosphate and is included in said emulsion composition in an amount ranging from about 0.1% to about 10% by weight of said composition.

44. The composition according to claim 41 wherein said neutralizing compound is selected from the group consisting of $Na_2HPO_4$, $K_2HPO_4$, $Na_3PO_4$, $K_3PO_4$, $NaHCO_3$, $KHCO_3$, $Na_2CO_3$, $K_2CO_3$ and mixtures thereof.

45. A method of producing an emulsion composition from an oil phase and a water phase, said oil phase comprising about 10% to about 90% by weight of said composition and said water phase comprising about 10% to about 90% by weight of said composition, said oil phase consisting essentially of about 70% to about 99.75% by weight of an oil and about 0.25% to about 30% by weight of a 12-hydroxystearic acid ester compound according to the formula:

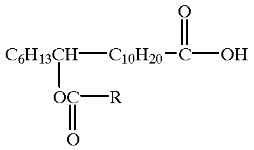

where R is a linear or branch chained saturated or unsaturated $C_6$–$C_{35}$ hydrocarbon group; said water phase consisting essentially of water and an amount of a neutralizing compound effective to produce an emulsion when said oil phase and said water phase are mixed, said method comprising, in any order, mixing said oil and said stearic acid ester compound at a temperature effective to form a solution of said oil phase;

mixing said water and said neutralizing compound at a temperature effective to form a solution of said water phase, and mixing said oil phase and said water phase at a temperature above about 75° C. to produce said emulsion.

46. The method according to claim 45 wherein each solution of said oil phase and said water phase are formed at an elevated temperature of at least about 70° C.

47. The method according to claim 45 where R is a $C_{11}$–$C_{23}$ hydrocarbon group.

48. The method according to claim 45 wherein said water phase is added to said oil phase and mixed for a period of at least about 10 minutes at a temperature of at least about 80° C. to produce said emulsion composition.

49. The method according to claim 45 wherein said neutralizing compound is selected from the group consisting of sodium tetraborate decahydrate, sodium tetraborate tetrahydrate, $Al(OH)_3$, $Ca(OH)_2$, $Mg(OH)_2$, $Na_2HPO_4$ or $K_2HPO_4Na_3PO_4$, $K_3PO_4$, $NaHCO_3$, $KHCO_3$, $Na_2CO_3$, $K_2CO_3$, NaOH, KOH, a fatty amine compound and mixtures thereof.

50. The method according to claim 45 wherein said neutralizing compound is selected from the group consisting of sodium tetraborate decahydrate and sodium tetraborate tetrahydrate.

51. The method according to claim 45 wherein said oil phase includes a secondary emulsifier in an amount ranging from about 0.1% to about 20% by weight of said oil phase.

52. The method according to claim 45 wherein said oil is a polar oil.

53. The method according to claim 51 wherein said secondary emulsifier is selected from the group consisting of polyethylene glycol 1500 dihydroxystearate and diethanolamine cetyl phosphate.

54. The method according to claim 51 wherein said neutralizing compound is selected from the group consisting of $Na_2HPO_4$, $K_2HPO_4$, $Na_3PO_4$, $K_3PO_4$, $NaHCO_3$, $KHCO_3$, $Na_2CO_3$, $K_2CO_3$ and mixtures thereof.

55. An emulsion composition produced by mixing an oil phase and a water phase, said oil phase comprising about 10% to about 90% by weight of said composition and said water phase comprising about 10% to about 90% by weight of said composition, said oil phase consisting essentially of at least about 70% to about 99.75% by weight of an oil and about 0.25% to about 30% by weight of 12-(behenoyloxy) stearic acid;

said water phase consisting essentially of water and an amount of a neutralizing compound effective to produce an emulsion when said oil phase and said water phase are mixed.

56. The composition according to claim 55 wherein said neutralizing compound is selected from the group consisting of sodium tetraborate decahydrate, sodium tetraborate tetrahydrate, $Al(OH)_3$, $Ca(OH)_2$, $Mg(OH)_2$, $Na_2HPO_4$ or $K_2HPO_4Na_3PO_4$, $K_3PO_4$, $NaHCO_3$, $KHCO_3$, $Na_2CO_3$, $K_2CO_3$, NaOH, KOH, a fatty amine compound and mixtures thereof.

57. The composition according to claim 55 wherein said fatty amine compound is a primary, secondary or tertiary amine compound containing at least one $C_{10}$ to $C_{22}$ alkyl, alkylene or substituted alkyl or alkylene group.

58. The composition according to claim 56 wherein said fatty amine contains at least one $C_{10}$ to $C_{22}$ alkyl group.

59. The composition according to claim 55 wherein said neutralizing compound is selected from group consisting of sodium tetraborate decahydrate and sodium tetraborate tetrahydrate, $Na_2HPO_4$, $K_2HPO_4Na_3PO_4$, $K_3PO_4$, $NaHCO_3$, $KHCO_3$, $Na_2CO_3$, $K_2CO_3$, NaOH, KOH and mixtures thereof.

60. The composition according to claim 55 wherein said oil comprises at least about 80% by weight of said oil phase and said stearic acid ester compound comprises no more than about 20% by weight of said oil phase.

61. The composition according to claim 55 wherein said oil phase further includes a secondary emulsifier in an emulsification effective amount.

62. The composition according to claim 61 wherein said oil is a polar oil.

63. The composition according to claim 61 wherein said secondary emulsifier is selected from the group consisting of polyethylene glycol 1500 dihydroxystearate and diethanolamine cetyl phosphate and is included in said emulsion composition in an amount ranging from about 0.1% to about 10% by weight of said composition.

64. The composition according to claim 55 wherein said neutralizing compound is selected from the group consisting of $Na_2HPO_4$, $K_2HPO_4$, $Na_3PO_4$, $K_3PO_4$, $NaHCO_3$, $KHCO_3$, $Na_2CO_3$, $K_2CO_3$ and mixtures thereof.

* * * * *